United States Patent [19]

Chang et al.

[11] Patent Number: 5,608,133
[45] Date of Patent: Mar. 4, 1997

[54] CATALYTIC OLIGOMERIZATION

[75] Inventors: Clarence D. Chang, Princeton; Tracy J. Huang, Lawrenceville, both of N.J.; Jose G. Santiesteban, Yardley; James C. Vartuli, West Chester, both of Pa.

[73] Assignee: Mobil Oil Corporation, Fairfax, Va.

[21] Appl. No.: 551,873

[22] Filed: Oct. 23, 1995

[51] Int. Cl.$^6$ ............................................ C07C 2/02
[52] U.S. Cl. .......................... 585/524; 585/502; 585/520; 585/523; 585/530; 585/531
[58] Field of Search ....................... 585/502, 520, 585/523, 524, 530, 531

[56] References Cited

U.S. PATENT DOCUMENTS

| | | |
|---|---|---|
| 3,960,978 | 6/1976 | Givens et al. . |
| 4,021,502 | 5/1977 | Plank et al. . |
| 4,150,062 | 4/1979 | Garwood et al. . |
| 4,211,640 | 7/1980 | Garwood et al. ........................ 208/25 |
| 4,227,992 | 10/1980 | Garwood et al. ........................ 208/46 |
| 5,098,684 | 3/1992 | Kresge et al. ............................ 423/277 |
| 5,113,034 | 5/1992 | Soled et al. .............................. 585/510 |
| 5,157,199 | 10/1992 | Soled et al. .............................. 585/750 |
| 5,171,905 | 12/1992 | Theriot et al. ............................ 585/10 |
| 5,345,026 | 9/1994 | Chang et al. ............................ 585/700 |
| 5,382,731 | 1/1995 | Chang et al. ............................ 585/315 |
| 5,401,478 | 3/1995 | Chang et al. ............................ 423/235 |
| 5,449,847 | 9/1995 | Chang et al. ............................ 585/266 |
| 5,453,556 | 9/1995 | Chang et al. ............................ 585/524 |

FOREIGN PATENT DOCUMENTS

| | | |
|---|---|---|
| 0585065 | 3/1994 | European Pat. Off. . |
| WO94/14732 | 7/1994 | European Pat. Off. . |
| 1-288339 | 1/1989 | Japan . |

OTHER PUBLICATIONS

Hino, M. et al., "Synthesis of Solid Superacid of Tungsten Oxide Supported Zirconia and Its Catalytic Action of Reactions of Butane and Pentane," J. Chem. Soc. Chem.Commun., 1259–1260 (1988).

Arata, K. and Hino, M., Proceedings 9th Intern. Congress On Catalysis, vol. 4, "Oxide Catalysts and Catalyst Development," M. J. Phillips et al., ed., 1727–1735 (1988).

Iglesia, E., Soled, S. L., and Kramer, G. M., Isomerization of Alkanes on Sulfated Zirconia: Promotion by Pt and by Adamantyl Hydride Transfer Species, Journal of Catalysis 144, 238–253 (1993).

Kirk–Othmer Encyclopedia of Chemical Technology, Third Ed., vol. 14, pp. 477–526.

Hsu, C.–Y., Heimbuch, C. R. Armes, C. T., and Gates, B. C., "A Highly Active Solid Superacid Catalyst for n–Butane Isomerization: A Sulfated Oxide Containing Iron, Manganese and Zirconium," J. Chem. Soc., Chem. Commun., 1645 (1992).

Primary Examiner—Glenn A. Caldarola
Assistant Examiner—E. D. Irzinski
Attorney, Agent, or Firm—Dennis P. Santini; Lori F. Cuomo

[57] ABSTRACT

There is provided a catalytic oligomerization process. The process involves the use of a catalyst comprising an acidic solid. The acidic solid may comprise a Group IVB metal oxide, such as zirconia, modified with an oxyanion of a Group VIB metal, such as tungsten. The oligomers produced by this process may be hydrogenated to produce thermally stable lubricants and lubricant additives, gasoline and diesel.

13 Claims, No Drawings

5,608,133

CATALYTIC OLIGOMERIZATION

CROSS REFERENCE TO RELATED APPLICATIONS

This application is related by subject matter to copending U.S. application Ser. No. 08/264,089, filed Jun. 22, 1994 and now U.S. Pat. No. 5,453,556.

FIELD OF THE INVENTION

There is provided an oligomerization process. The process involves the use of a catalyst comprising an acidic solid. The acidic solid may comprise a Group IVB metal oxide, such as zirconia, modified with an oxyanion of a Group VIB metal, such as tungsten. The oligomers produced by this process may be hydrogenated to produce thermally stable lubricants and lubricant additives.

BACKGROUND OF THE INVENTION

Conversion of olefins to gasoline and/or distillate products is disclosed in U.S. Pat. Nos. 3,960,978 and 4,021,502 wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992, Garwood and Lee disclose the operating conditions for the Mobil Olefin to Gasoline/Distillate (MOGD) process for selective conversion of $C_3^+$ olefins to mainly aliphatic hydrocarbons. In a related manner, U.S. Pat. Nos. 4,150,062 and 4,211,640 disclose a process for converting olefins to gasoline components.

Dimerization of propene with impregnated $ZrO_2/SO_4$ or $ZrO_2/WO_3$ catalysts is described in U.S. Pat. No. 5,113,034.

Efforts to improve upon the performance of natural mineral oil based lubricants by the synthesis of oligomeric hydrocarbon fluids have been the subject of important research and development in the petroleum industry for a large number of years and have led to the introduction of a number of superior polyalpha-olefin (PAO) synthetic lubricants produced by the oligomerization of alpha-olefins or 1-alkenes. In terms of lubricant property improvement, the thrust of the industrial research effort on synthetic lubricants has been toward fluids exhibiting useful viscosities over a wider range of temperature, i.e., improved viscosity index (VI), while also showing lubricity, thermal and oxidative stability and pour point equal to or better than mineral oil. These new synthetic lubricants exhibit lower friction characteristics and are therefore capable of increasing mechanical efficiency of various types of equipment including engines, transmissions, worm gears and traction drives, doing so over a wider range of operating conditions than mineral oil lubricants.

PAO lubricants are often formulated with additives to enhance those properties for specific applications. Among the more commonly used additives are oxidation inhibitors, rust inhibitors, metal passivators, antiwear agents, extreme pressure additives, pour point depressants, detergent-dispersants, viscosity index (VI) improvers, foam inhibitors and the like. This aspect of lubricant technology is described in *Kirk-Othmer Encyclopedia of Chemical Technology*, 3rd ed., 14, 477–526, to which reference is made for a description of the use of such additives.

PAOs useful as synthetic base stocks or functional fluids may be synthesized by homogeneous catalysts, such as promoted $BF_3$ or $AlCl_3$ catalysts. The synthesis of PAOs with a promoted BF catalyst is discussed in the Theriot et al. U.S. Pat. No. 5,171,905. The PAO processes using homogeneous catalysts always include a complicated and tedious catalyst separation step. For example, the promoted $BF_3$ or $AlCl_3$ catalyst is usually deactivated and destroyed by washing with sodium hydroxide, dilute acid and water consecutively. This separation step generates waste and is tedious. Therefore, it would be advantageous to use a solid and regenerable catalyst which can be separated easily from product and regenerated for reuse.

SUMMARY OF THE INVENTION

There is provided a process for oligomerizing olefins, said process comprising contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by coprecipitating the Group IVB metal oxide along with the oxyanion of the Group VIB metal.

There is further provided a process for producing a synthetic lubricant composition, said process comprising the steps of:

(a) contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating the Group IVB metal oxide along with the oxyanion of the Group VIB metal;

(b) distilling the product of step (a) under conditions sufficient to remove unreacted olefin monomer and $C_{20}$-oligomers therefrom; and (c) hydrogenating the $C_{20}+$ oligomers from step (b) under conditions sufficient to remove olefinic unsaturation therefrom.

There is further provided a process for producing a gasoline or gasoline blending stock, the process comprising contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating a Group IVB metal oxide along with an oxyanion of a Group VIB metal.

There is further provided a process for producing a diesel or diesel blending fuel blending stock, the process comprising contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating the Group IVB metal oxide along with the oxyanion of the Group VIB metal.

DETAILED DESCRIPTION OF THE PRESENT INVENTION

The present invention is particularly useful for upgrading $C_2$–$C_5$ lower olefins to heavier hydrocarbons, such as $C_6$–$C_{20}+$ gasoline and distillate fuel product. Numerous mono-olefins, including ethene, propene, n-butenes, isobutene, pentenes, hexenes, mixtures thereof, etc., can be reacted selectively in aliphatic hydrocarbon feedstocks. An advantage of the present process is reaction selectivity, such that non-olefinic products can be avoided as reaction byproducts, due to the substantial absence of dehydrogenation, cyclization and alkane formation. However, the feedstocks may contain non-deleterious amounts of paraffins.

In a preferred embodiment, the catalyst of the present invention is employed in the conversion of propene by oligomerization to gasoline, diesel fuel and lube coproducts. Preferred propene feedstocks include propene and FCC propane/propene. N-butane and butenes can also be included in the feed. Optionally, hydrogen can be cofed into the reactor with the hydrocarbon feed.

Oligomerization reaction temperature is in the range of from about 25° to about 400° C. and preferably in the range of from about 100° to about 220° C. Pressure is in the range of from about 0 to about 2000 psig. The reaction may be conducted in the gas phase, liquid phase or dense phase with continuous or batch operation using, for example, a fixed bed or stirred-tank reactor. Generally, the liquid hourly space velocity, based on volume of liquid olefin per volume of catalyst per hour, is in the range of about 0.1–10, preferably 0.5–3.

The product slates can be adjusted by varying the operation conditions. The coproduction of gasoline and diesel is favored by higher temperatures (120°–350° C.) and lower pressures (30–1000 psig) in the above ranges. The coproduction of gasoline, diesel and lube is favored by lower temperatures (30°–250° C.) and higher pressures (300–2000 psig) in the above ranges. In cases when an increased amount of lube fraction is desirable, part of the oligomer product (e.g., $C_{19}$- or $C_{10}$-) can be recycled to the reactor.

The deactivated catalyst can be hydrogenatively regenerated in the presence of hydrogen or oxidatively regenerated in the presence of air.

The acidic solid material useful as a catalyst in the present process may be prepared in accordance with U.S. Pat. Ser. No. 08/236,073, filed May 2, 1994, the entire disclosure incorporated herein by reference.

The solid material described herein comprises an oxide of a Group IVB metal, preferably zirconia or titania. This Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, Volume 4, pages 1727–1735(1988), the entire disclosures of these publications are expressly incorporated herein by reference. According to these publications, tungstate is impregnated onto a preformed solid zirconia material.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in Proceedings *9th International Congress on Catalysis*, Volume 4, pages 1727–1735(1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure. It is further suggested that the tungsten oxide combines with zirconium oxide compounds to create superacid sites at the time the tetragonal phase is formed.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Suitable sources of the Group IVB metal oxide, used for preparing the catalyst, include compounds capable of generating such oxides, such as oxychlorides, chlorides, nitrates, oxynitrates, etc., particularly of zirconium or titanium. Alkoxides of such metals may also be used as precursors or sources of the Group IVB metal oxide. Examples of such alkoxides include zirconium n-propoxide and titanium i-propoxide. These sources of a Group IVB metal oxide, particularly zirconia, may form zirconium hydroxide, i.e., $Zr(OH)_4$, or hydrated zirconia as intermediate species upon precipitation from an aqueous medium in the absence of a reactive source of tungstate. The expression, hydrated zirconia, is intended to connote materials comprising zirconium atoms covalently linked to other zirconium atoms via bridging oxygen atoms, i.e., Zr—O—Zr, further comprising available surface hydroxy groups. When hydrated zirconia is impregnated with a suitable source of tungstate under sufficient conditions, these available surface hydroxyl groups are believed to react with the source of tungstate to form an acidic catalyst. As suggested in the aforementioned article by K. Arata and M. Hino in *Proceedings 9th International Congress on Catalysis*, Volume 4, pages 1727–1735 (1988), precalcination of $Zr(OH)_4$ at a temperature of from about 100° C. to about 400° C. results in a species which interacts more favorably with tungstate upon impregnation therewith. This precalcination is believed to result in the condensation of ZrOH groups to form a polymeric zirconia species with surface hydroxyl groups. This polymeric species is referred to herein as a form of a hydrated zirconia.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The present modified oxide material may be prepared by combining a first liquid solution comprising a source of a Group IVB metal oxide with a second liquid solution comprising a source of an oxyanion of a Group VIB metal. This combination of two solutions takes place under conditions sufficient to cause co-precipitation of the modified oxide material as a solid from the liquid medium. Alternatively, the source of the Group IVB metal oxide and the source of the oxyanion of the Group VIB metal may be combined in a single liquid solution. This solution may then be subjected to conditions sufficient to cause co-precipitation of the solid modified oxide material, such as by the addition of a precipitating reagent to the solution. Water is a preferred solvent for these solutions.

The temperature at which the liquid medium is maintained during the co-precipitation may be less than about 200° C., e.g., from about 0° C. to about 200° C. This liquid medium may be maintained at an ambient temperature (i.e., room temperature) or the liquid may be cooled or heated. A particular range of such temperatures is from about 10° C. to about 100° C.

The liquid medium from which the present catalyst components are co-precipitated may optionally comprise a solid support material, in which case the present catalyst may be co-precipitated directly onto the solid support material. Examples of such support materials include the material designated M41S, which is described in U.S. Pat. No. 5,102,643. A particular example of such an M41S material is a material designated MCM-41, which is described in U.S. Pat. No. 5,098,684.

Support materials and/or co-catalyst materials may also, optionally, be co-precipitated from the liquid medium along with the Group IVB metal oxide and the oxyanion of the Group VIB metal. An example of a co-catalyst material is a hydrogenation/dehydrogenation component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., oligomerization.

The modified acidic oxide may be contacted with hydrogen at elevated temperatures. These elevated temperatures may be 100° C. or greater, e.g., 250° C. or greater, e.g., about 300° C. The duration of this contact may be as short as one hour or even 0.1 hour. However, extended contact may also be used. This extended contact may take place for a period of 6 hours or greater, e.g., about 18 hours. When zirconia is modified with tungstate and then contacted with hydrogen at elevated temperatures, an increase in catalytic activity, e.g., for paraffin isomerization, has been observed. The modified acidic oxide may be contacted with hydrogen in the presence or absence of a hydrocarbon cofeed.

The present modified oxide material may be recovered by filtration from the liquid medium, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.1–24 hours, and more preferably for about 1.0–10 hours. In a most preferred embodiment, calcination is carried out at about 800° C. for about 1 to about 3 hours.

In the present catalyst, of the Group IVB oxides, zirconium oxide is preferred and of the Group VIB anions, tungstate is preferred.

Qualitatively speaking, elemental analysis of the present acidic solid will reveal the presence of Group IVB metal, Group VIB metal and oxygen. The amount of oxygen measured in such an analysis will depend on a number of factors, such as the valence state of the Group IVB and Group VIB metals, the form of the optional hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The present catalyst is acidic and may be observed as being highly acidic, even to the extent of being a superacid. Superacids are a known class of acidic materials which have an acidity greater than that of 100% $H_2SO_4$. This level of acidity may be determined by any appropriate means, including the use of suitable indicators, the determination of the ability to protonate certain chemicals, and/or the determination of the ability to stabilize certain cations, especially certain carbonium or carbenium ions. For example, this catalyst, whether analyzed in the presence or absence of optional components (e.g., hydrogenation/dehydrogenation components) and/or binder materials, may have an acid strength of a superacid as measured by the color change of an appropriate indicator, such as the Hammett indicator. More particularly, the Ho acid strength of the present catalyst may have a value of less than −13, i.e., an "acid strength" of greater than −1339. The use of Hammett indicators to measure the acidity of solid superacids is discussed in the Soled et al. U.S. Pat. No. 5,157,199. This Soled et al. patent also describes the Ho acid strength for certain sulfated transition metal superacids.

The following examples illustrate the process of the present invention.

EXAMPLE 1

Five hundred grams of $ZrOCl_2 \cdot 8H_2O$ were dissolved with stirring in 7.0 liters of distilled water. A solution containing 263 ml of conc. $NH_4OH$, 500 ml of distilled water, and 54 grams of $(NH_4)_6H_2W_{12}O_{40} \cdot xH_2O$ was added dropwise over 30–45 minute period. The pH of the solution was adjusted to approximately 9 (if needed) by adding additional conc. $NH_4OH$ dropwise. This slurry was then placed in the steambox for 72 hours. The product formed was recovered by filtration, washed with excess $H_2O$, and dried overnight at 85° C. The material was then calcined in dry air at 825° C. for 3 hours. The resulting binary oxide catalyst contained 15.9 wt. % of W and 58.6 wt. % of Zr. This co-precipitated $WOx/ZrO_2$ catalyst is called Catalyst A.

EXAMPLE 2

7.0 cc (9.28 g) of Catalyst A (30–60 mesh particles) was charged to a fixed-bed tubular reactor. The catalyst was calcined with flowing air at 500° C. and 1 atm for an hour, and the purged with $N_2$ for 30 minutes. The temperature was decreased to 350° C., and the catalyst was reduced with flowing $H_2$ at 350° C. and 1 atmosphere atm for one hour. The reactor was then purged with $N_2$ for one hour and the temperature was reduced to 120° C. At this stage, the reactor was pressurized with $N_2$ to 400 psig and propene was fed into the reactor at a rate of 7 ml/hour. Then, the reactor temperature was gradually increased to 160° C. After the system was lined out overnight, a material balance was conducted over a 6 hour period. The product analysis by gas chromatography showed that the propene conversion was 94.4 wt. % with a $C_5+$ selectivity of 94.9 wt. %. The $C_5+$ products contained 29.5 wt. % of gasoline ($C_5$–330° F.), 61.6 wt. % of diesel fuel (330°–650° F.), and 8.9 wt. % of lube (650° F.+).

EXAMPLE 3

One part by weight of zirconyl chloride, $ZrOC_{12} \cdot H_2O$, was added to 3 parts by weight of a 10 M $NH_4OH$ solution. The resulting slurry, $Zr(OH)_4$, was filtered and washed with 5 parts by weight of distilled deionized water, then air dried at 140° C. for 8 hours. Approximately 5.5 parts by weight of the resulting $Zr(OH)_4$ were impregnated via incipient wetness with 2.2 parts of an aqueous solution containing 1 part of ammonium metatungstate, $(NH_4)_6H_2W_{12}O_{40} \cdot xH_2O$ The resulting material was dried for 2 hours at 120° C. and then calcined at 825° C. in flowing air for 3 hours. This impregnated $WO_x/ZrO_2$ catalyst, called Catalyst B, contained 15 wt. % W.

EXAMPLE 4

6.5 cc (9.30 g) of Catalyst B (30–60 mesh particles) were charged to a fixed-bed tubular reactor. The catalyst was calcined with flowing air at 500° C. and 1 atm for an hour, and then purged with $N_2$ for 30 minutes. The temperature was decreased to 350° C., and the catalyst was reduced with flowing $H_2$ at 350° C. and 1 atm for one hour. The reactor was then purged with $N_2$ for one hour and the temperature was reduced to 120° C. At this stage, the reactor was pressurized with $N_2$ to 400 psig and propene was fed into the reactor at a rate of 7 ml/hour. Then, the reactor temperature was gradually increased to 160° C. After the system was lined out overnight, a material balance was conducted over a 6 hour period. The product analysis by gas chromatography showed that the propene conversion was 69.8 wt. % with a selectivity of 93.0 wt. %. The $C_5+$ products contained 38.5 wt. % of gasoline ($C_5$–330° F.), 56.0 wt. % of diesel fuel (330°–650° F.), and 5.5 wt. % of lube (650° F.+).

The comparison between the co-precipitated catalyst (Catalyst A) and the impregnated catalyst (Catalyst B) for propene oligomerization under the same operating conditions are given below:

| Catalyst | Catalyst A | Catalyst B |
| --- | --- | --- |
| Method of Preparation | Co-Precipitation | Impregnation |
| Propylene Conversion, % | 94.4 | 69.8 |
| $C_5+$ Selectivity, wt. % | 94.9 | 93.0 |
| $C_5+$ Distribution, wt. % | | |
| Gasoline ($C_5$–330° F.) | 29.5 | 38.5 |
| Diesel (330°–650° F.) | 61.6 | 56.0 |
| Lube (650° F.+) | 8.9 | 5.5 |

The above comparison clearly indicates that the co-precipitated catalyst is more active than the impregnated catalyst, as reflected by the higher propene conversion and higher yields of diesel and lube.

EXAMPLE 5

Five hundred grams of $ZrOCl_2 \cdot 8H_2O$ were dissolved with stirring in 7.5 liters of distilled water. 263 grams of conc. $NH_4OH$ were added dropwise over a 30–45 minute period to precipitate the $Zr(OH)_4$ and adjust the pH to approximately 9. The product was recovered by filtration, washed with excess water, and dried overnight at 95° C. A solution of 54 grams of $(NH_4)_6H_2W_{12}O_{40} \cdot xH_2O$ dissolved in 100 ml of $H_2O$ was then impregnated on this dried product. Finally, the tungsten containing product was dried overnight at ~95° C. and then calcined in air at 825° C. for 3 hours. The resulting binary oxide catalyst contained 17.8 wt. % of W and 56.4 wt. % of Zr. This impregnated $WO_x/ZrO_2$ catalyst is called Catalyst C.

EXAMPLE 6

Catalyst A and Catalyst C were tested in a fixed-bed reactor for n-pentane hydrocracking to determine their relative acidity. The operating conditions were 232° C., 350 psig, 2 LHSV and 2 $H_2/n-C_5$. The results are given below:

| Catalyst | A | C |
| --- | --- | --- |
| Total $C_5$ Conversion, wt. % | 27.7 | 10.3 |
| Product Distribution, wt. % | | |
| $C_1 + C_2$ | 0.8 | 1.0 |
| $C_3$ | 2.5 | 1.2 |
| $C_4$ | 21.4 | 6.6 |
| $C_5$ | 72.3 | 89.7 |
| $C_6+$ | 2.9 | 1.4 |
| $C_4^-$ yield, wt. % | 24.7 | 8.8 |

The higher catalytic activity for Catalyst A, as evidenced by the higher $C_4^-$ yield, indicates that Catalyst A has higher acidity than Catalyst C. Catalyst A results in enhanced cracking selectivity which indicates increased acidity which is useful for oligomerization.

Changes and modifications in the specifically described embodiments can be carried out without departing from the scope of the invention which is intended to be limited only by the scope of the appended claims.

What is claimed is:

1. A process for oligomerizing olefins, said process comprising contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating the Group IVB metal oxide along with the oxyanion of the Group VIB metal.

2. A process according to claim 1, wherein the olefin comprises propene.

3. A process according to claim 1, wherein the olefin comprises butenes.

4. A process according to claim 1, wherein said Group IVB metal is Zr and wherein said Group VIB metal is W.

5. A process according to claim 1, wherein said oligomerization reaction conditions include a temperature in the range of from about 25° to about 400° C. and a pressure in the range of from about 0 to about 2000 psig.

6. A process for producing a synthetic lubricant composition, said process comprising the steps of:
   (a) contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating the Group IVB metal oxide along with the oxyanion of the Group VIB metal;
   (b) distilling the product of step (a) under conditions sufficient to remove unreacted olefin monomer and $C_{20}$-oligomers therefrom; and
   (c) hydrogenating the $C_{20}+$ oligomers from step (b) under conditions sufficient to remove olefinic unsaturation therefrom.

7. A process according to claim 6, wherein said Group IVB metal is Zr and wherein said Group VIB metal is W.

8. A process according to claim 6, in which the oligomerization is carried out at a temperature of from 25° to 400° C.

9. A process for producing a gasoline or gasoline blending stock, the process comprising contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating a Group IVB metal oxide along with an oxyanion of a Group VIB metal.

10. A process according to claim 9, wherein said Group IVB metal is Zr and wherein said Group VIB metal is W.

11. A process for producing a diesel or diesel blending stock, the process comprising contacting at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating the Group IVB metal oxide along with the oxyanion of the Group VIB metal.

12. A process for co-producing a gasoline and diesel, the process comprising contacting, at a temperature in the range of from about 120° to about 350° C. and at a pressure in the range of from about 30 to about 1000 psig, at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating a Group IVB metal oxide along with an oxyanion of a Group VIB metal.

13. A process for co-producing a gasoline, diesel and lube, the process comprising contacting, at a temperature in the range from about 30° to about 250° C. and at a pressure in the range of about 300 to about 2000 psig, at least one olefin having less than 6 carbon atoms under sufficient oligomerization reaction conditions with a catalyst comprising an acidic solid comprising a Group IVB metal oxide modified with an oxyanion of a Group VIB metal, said catalyst prepared by co-precipitating a Group IVB metal oxide along with an oxyanion of a Group VIB metal.

\* \* \* \* \*